United States Patent [19]
Bynon et al.

[11] Patent Number: 5,667,523
[45] Date of Patent: Sep. 16, 1997

[54] DUAL SUPPORTED INTRALUMINAL GRAFT

[75] Inventors: Anne Nina Bynon, Tolleson; Sandra M. Cundy, Mesa; Rajagopal R. Kowligi, Phoenix, all of Ariz.

[73] Assignee: Impra, Inc.

[21] Appl. No.: 430,970

[22] Filed: Apr. 28, 1995

[51] Int. Cl.⁶ .................................. A61M 29/00
[52] U.S. Cl. ............... 606/198; 606/194; 623/1; 623/12
[58] Field of Search ............... 606/192, 194, 606/195, 198, 153–156, 191; 623/1, 12

[56] References Cited

U.S. PATENT DOCUMENTS

| | | | |
|---|---|---|---|
| 4,604,762 | 8/1986 | Robinson | 623/1 |
| 4,705,517 | 11/1987 | DiPisa, Jr. | 623/12 |
| 4,728,328 | 3/1988 | Hughes et al. | 623/12 |
| 4,731,073 | 3/1988 | Robinson | 623/1 |
| 4,769,029 | 9/1988 | Patel | 623/1 |
| 4,787,899 | 11/1988 | Lazarus | 623/1 |
| 4,850,999 | 7/1989 | Planck | 623/1 |
| 5,064,435 | 11/1991 | Porter | 623/12 |
| 5,078,726 | 1/1992 | Kreamer | 606/194 |
| 5,084,065 | 1/1992 | Weldon et al. | 623/1 |
| 5,123,917 | 6/1992 | Lee | 623/1 |
| 5,151,105 | 9/1992 | Kwan-Gett | 623/1 |
| 5,156,620 | 10/1992 | Pigott | 623/1 |
| 5,163,951 | 11/1992 | Pinchuk et al. | 623/1 |
| 5,207,695 | 5/1993 | Trout, III | 606/153 |
| 5,211,658 | 5/1993 | Clouse | 623/1 |
| 5,219,355 | 6/1993 | Parodi et al. | 606/191 |
| 5,236,447 | 8/1993 | Kubo et al. | 623/1 |
| 5,258,027 | 11/1993 | Berghaus | 623/9 |
| 5,282,860 | 2/1994 | Matsuno et al. | 623/12 |
| 5,306,294 | 4/1994 | Winston et al. | 623/1 |
| 5,330,490 | 7/1994 | Wilk et al. | 606/153 |
| 5,330,500 | 7/1994 | Song | 606/198 |
| 5,330,528 | 7/1994 | Lazim | 623/1 |
| 5,334,201 | 8/1994 | Cowan | 623/1 |
| 5,366,473 | 11/1994 | Winston et al. | 606/198 |
| 5,380,328 | 1/1995 | Morgan | 606/70 |

*Primary Examiner*—Michael Buiz
*Assistant Examiner*—Patrick W. Rasche
*Attorney, Agent, or Firm*—David G. Rosenbaum

[57] ABSTRACT

A dual supported intraluminal graft comprising a biocompatible flexible layer sandwiched between two structural support layers. The preferred embodiment comprises a first structural support, such as a stent, which is concentrically retained within a tubular shaped PTFE graft which is concentrically retained within a second structural support, such as a stent. The ends of the PTFE graft may be folded back onto the outer surface of the second structural support thereby forming flaps. Upon radial expansion of the preferred embodiment, the stent/graft/stent assembly forms inseparable layers.

22 Claims, 5 Drawing Sheets

DUAL SUPPORTED INTRALUMINAL GRAFT

FIELD OF THE INVENTION

The present invention relates generally to an intraluminal graft which comprises a polytetrafluoroethylene (PTFE) material sandwiched between two similar structural support materials such as those materials which comprise stents. The stent materials include any suitable material having the strength and elasticity to permit radial expansion and resist radial collapse such as silver, titanium, stainless steel, gold, or any suitable plastic material having the required strength and elasticity as previously described. More particularly, one preferred embodiment of the present invention relates to a balloon expandable intraluminal vascular graft which includes a PTFE tubular graft that is sandwiched between two radially expandable stents. Other embodiments of the invention include, but are not limited to, a tubular configuration having an unsupported flexible graft section between dual supported ends, an articulated tubular configuration, and a bifurcated tubular configuration. The dual supported intraluminal graft may be used in both vascular and non-vascular applications to eliminate obstructed areas. Contemplated non-vascular applications include, but are not limited to, esophageal stenosis, prostatic hyperplasia and constricted fallopian tubes. The present invention is further directed to a method for producing the double stented intraluminal graft.

DESCRIPTION OF THE PRIOR ART

Radially expandable stents are used to maintain an occluded anatomical passageway in an unoccluded state and are well known in the art of vascular prostheses. The use of radially expandable stents in endovascular applications is exemplified in U.S. Pat. No. 4,733,665 issued to Palmaz and U.S. Pat. No. 4,580,568 issued to Gianturco.

The prior art in the field of the invention includes numerous stent/graft combinations. For example, the Parodi, et al. patent, U.S. Pat. No. 5,219,355, discloses a balloon device for implanting an aortic intraluminal prosthesis for repairing aneurysms which utilizes a catheter having two inflatable balloons to expand two stents which are sutured to opposite ends of a flexible dacron graft. The main purpose of the stents is to facilitate securing and anchoring the graft to the wall of the blood vessel. The Kreamer patent, U.S. Pat. No. 5,078,726, describes a method and apparatus for repairing a weakened blood vessel section which includes a pair of expandable stents that are placed on the inside ends of a flexible vascular graft. The graft/stent ends of the resulting prosthesis are positioned on the weakened sides of the blood vessel and expanded to frictionally secure the graft within the vessel. The purpose of the Kreamer method and apparatus is to provide structural support to the ends of the resulting graft which further facilitates anchoring the ends of the resulting graft to a blood vessel.

Other means for supplying structural support and stability to the ends of a flexible vascular graft are also known in the prior art. For example, the Hughes, et al. patent, U.S. Pat. No. 4,728,328, discloses a cuffed tubular vascular prosthesis. The prosthesis is formed by coating a mandrel with a polymer solution, air-curing the coating, removing the prosthesis from the mandrel, turning the prosthesis inside out, folding back the edges of the prosthesis over itself, and bonding the turned back edges to the body of the prosthesis. A double cuffed prosthesis may also be formed by sliding a suture sleeve over the prosthesis cuff, folding the sleeve back over itself, and bonding its turned over edges to the prosthesis cuff and tubular body. This graft configuration minimizes infection and tissue granulation at the anastomosis, and maximizes long term stability when the ends of the blood vessel are pulled over and sutured to the prosthesis cuffs. The Patel patent, U.S. Pat. No. 4,769,029, discloses another type of structural support and anchoring device located at the ends of a flexible tubular graft. The Patel prosthesis describes an anchoring device attached at opposite ends of a flexible tube member where each anchoring device comprises a ring member, a circular member spaced a predetermined distance apart from the ring member, and a connecting member which attaches the ring and circular members. Each ring member is connected to, and defines an opening into, an opposite end of the flexible tube member.

More recently, the field of prior art has advanced to provide structural support to other areas of the flexible vascular graft, including mid portions and entire surface areas of the graft, in addition to just the end portions of the vascular graft. For example, U.S. Pat. No. 5,211,658 issued to Clouse discloses a device for repairing aneurysms which comprises at least a percutaneously-insertable structural frame, a flexible thin-walled tubular member placed within the structural frame, and means for expanding and holding the flexible tubular member adjacent the inside of the structural frame. Further, the Song patent, U.S. Pat. No. 5,330,500, discloses a radially expandable stent having an outer surface wrapped with mesh. The mesh is then coated with a silicon rubber which prevents cancer cells from penetrating into the stent.

Finally, recent improvements have been made in the area of structurally supported grafts which include grafts that comprise overlapping stents or similar types of structural supports. For instance, U.S. Pat. No. 5,064,435 issued to Porter discloses a self-expanding prosthesis comprising two or more generally tubular, coaxial and slidably connected stent segments. The axially outward and non-overlapping portions of the stent may be used to facilitate fixation of the prosthesis to the blood vessel. Alternatively, reinforcing segments may be positioned near the opposite ends of the stent in order to maintain the axial length of the prosthesis during expansion.

Also, the Morgan patent, U.S. Pat. No. 5,380,328, discloses a composite perforated implant structure which comprises at least one biologically and chemically inert microporous membrane which is supported by at least one layer of perforated, biocompatible metallic sheet material. The microporous membrane is preferably comprised of randomly dispersed PTFE fibers, mixtures of cellulose acetate and cellulose nitrate fibers, or polyvinylidine difluoride fibers. The Morgan patent also discloses an implant structure which includes two layers of perforated, biocompatible metallic sheet material wherein one layer is affixed to each side of the biologically and chemically inert microporous membrane.

Although the prior art addresses some of the specific problems associated with flexible vascular grafts such as the need for minimally invasive procedures and devices for repairing blood vessels, the need for structural support of the graft particularly at its ends in order to facilitate anchoring the graft to the blood vessel, and the desire to maintain the axial length of the graft, the prior art does not address the need for the continuous uniform expansion of the graft during dilatation of the graft for endovascular or intraluminal application. Further, the prior art does not disclose a monolithic device for endovascular or intraluminal application which comprises inseparable component layers that serve to mimic the function of a blood vessel in vivo. The prior art also fails to disclose a vascular graft having a structural composition which allows the final expansion diameter of the graft to increase without increasing the introducer sheath size.

Accordingly, there is a need for a vascular graft having a structural configuration which provides for all of the previously described necessities in order to provide a compact, durable and easily implantable vascular graft.

SUMMARY OF THE INVENTION

It is a principal object of the present invention to provide a intraluminal graft having dual support members.

It is a further object of the present invention to provide an expandable intraluminal graft that can be used with any conventional balloon catheter and which easily detaches from the balloon catheter upon deflation of the balloon without exhibiting recoil of the graft onto the balloon.

It is still a further object of the present invention to provide a one-piece expandable intraluminal graft which comprises a polytetrafluoroethylene layer and dual support layers which are inseparable both in vitro and in vivo.

It is yet a further object of the present invention to provide an expandable intraluminal graft which can perform uniform radial expansion upon inflation of the expandable intraluminal graft with any conventional balloon catheter.

It is a still further object of the present invention to provide an intraluminal graft that has increased durability over prior art intraluminal grafts.

It is yet another object of the present invention to provide an expandable intraluminal graft which produces anchoring points at its ends upon expansion of the graft in vivo for securing the graft to a blood vessel wall.

It is still another object of the present invention to provide an intraluminal graft having increased radiopacity thereby enabling its position to be easily localized.

It is another object of the present invention to provide an expandable intraluminal graft whose final expansion diameter can be increased without increasing the size of the introducer sheath.

It is yet another object of the present invention to provide an expandable dual supported intraluminal graft having a tubular shaped polytetrafluoroethylene graft sandwiched between two stents wherein the stents and polytetrafluoroethylene graft form inseparable layers.

It is yet another object of the present invention to provide an expandable dual supported intraluminal graft whose final expansion length exhibits no foreshortening or compression of the graft away from the ends.

Briefly, the present invention generally comprises an expandable dual supported intraluminal graft which comprises a first layer of support material, a second layer of support material directly overlapping the first layer of support material, and a biocompatible flexible layer sandwiched between the first and second layers of support material wherein at least a portion of the biocompatible flexible layer is folded back onto at least one of the support layers. The support layers are preferably comprised of a strong material which resists radial collapse such as silver, titanium, stainless steel, gold, or any suitable plastic material having the necessary strength and elasticity to enable uniform expansion without collapse. The biocompatible flexible layer is preferably comprised of expanded polytetrafluoroethylene.

A preferred embodiment of the expandable dual supported endovascular or intraluminal graft includes a first tubular shaped support member having an inner surface and an outer surface, a second tubular shaped support member having an inner surface and an outer surface wherein the first tubular shaped support member is concentrically positioned within the second tubular shaped support member, and a biocompatible flexible tubular member sandwiched between the first and second tubular shaped members such that the outer surface of the biocompatible flexible tubular member lies adjacent to the inner surface of the second tubular shaped support member and the inner surface of the biocompatible flexible tubular member lies adjacent to the outer surface of the first tubular shaped support member.

The second tubular shaped support member in the preferred embodiment may comprise first and second cylindrical shaped support members which are designed to be positioned so that each cylindrical support member overlaps the first tubular shaped support member at one of its ends. This configuration of the second tubular shaped support member results in a intraluminal graft having a first tubular support member, a flexible biocompatible tubular member positioned over the first tubular support member which is at least as long as the first tubular support member, and two shorter cylindrical shaped support members positioned over the flexible biocompatible tubular member near each of its ends, respectively. Accordingly, there is no dual support at the center of the intraluminal graft. Instead, only one support member, namely the first tubular shaped support member, provides support to the flexible biocompatible member at the center of the graft.

In addition, the first tubular shaped support member in the preferred embodiment may also comprise a set of two shorter cylindrical shaped support members which are designed to be positioned such that the two shorter cylindrical shaped support members which comprise the second tubular shaped support member directly overlap the two cylindrical shaped support members which comprise the first tubular shaped support member. In the preferred embodiment, the tubular shaped support members preferably comprise stents like those previously described in reference to Palmaz, U.S. Pat. No. 4,733,665, and Gianturco, U.S. Pat. No. 4,580,568. Further, the use of a spring or spring-like structure for the tubular shaped support members is also contemplated. The flexible biocompatible tubular member is preferably comprised of expanded polytetrafluoroethylene. When the first tubular shaped support member also comprises two shorter cylindrical shaped supports, like the second tubular shaped support member described above, the resulting configuration is a vascular graft comprising a PTFE tube having double stents located at each end of the tube, one stent on the outside of the PTFE tube and one stent on the inside of the PTFE tube, thereby leaving the center section of the PTFE tube unsupported. The present invention also contemplates an intraluminal graft having double stents sandwiching a PTFE tube wherein the double stents are located at only one end of the intraluminal graft.

Further, the ends of the biocompatible flexible tubular layer in the above described preferred embodiment may be folded back against the outer surface of the second tubular shaped support member so that the ends of the second tubular shaped support member are encased within the biocompatible flexible tubular member. Where the second tubular shaped support member comprises first and second shorter cylindrical shaped support members, the ends of the flexible biocompatible tubular member may be folded back onto the shorter cylindrical shaped support members such that at least one end of each of the shorter cylindrical members is encased within the flexible biocompatible tubular member. This additional structural element of the device creates a vascular prosthesis having a stent/graft combination which enables uniform radial expansion from the center outward with any conventional balloon catheter without requiring suturing of the graft and stent components to one another.

Also, both the first and second tubular shaped support members in the preferred embodiment may each comprise a series of shortened cylindrical support members which thereby form multiple pairs of directly overlapping cylindrical support members with gaps between each overlapping pair to allow flexibility along the length of the graft. Each pair of overlapping cylindrical support members contains a portion of the biocompatible flexible tubular layer sandwiched between them. The resulting configuration is an intraluminal graft having double stents at each end of the graft for anchoring, with alternating areas of dual support members for increased durability, and alternating areas of unsupported graft for flexibility in both delivery and deployment of the graft.

The present invention is also directed to a process for making an expandable dual supported intraluminal graft which includes the steps of:

a) positioning a biocompatible flexible tubular member having an inner surface and an outer surface over a first tubular shaped support member having an inner surface and an outer surface such that the inner surface of said biocompatible flexible tubular member lies adjacent to the outer surface of said first tubular shaped support member;

b) positioning a second tubular shaped support member having an inner surface and an outer surface directly over the outer surface of said biocompatible flexible tubular member such that the outer surface of said biocompatible flexible tubular member is adjacent the inner surface of said second tubular shaped support member and said biocompatible flexible tubular member is sandwiched between said first and second tubular shaped support members; and c) applying a positive pressure to said biocompatible flexible tubular member and said first and second tubular shaped support members such that all of said members are inseparable.

The process may further include the step of folding the ends of the biocompatible flexible tubular member back over the ends of the second tubular shaped support member and onto the outer surface of the second tubular shaped support member thereby encasing the ends of the second tubular shaped support member within the biocompatible flexible tubular member.

These and other objects, features and advantages of the present invention will become more apparent to those skilled in the art when taken with reference to the following more detailed description of the preferred embodiments of the invention in conjunction with the accompanying drawings.

DETAILED DESCRIPTION OF THE PREFERRED EMBODIMENTS

Figure 1:
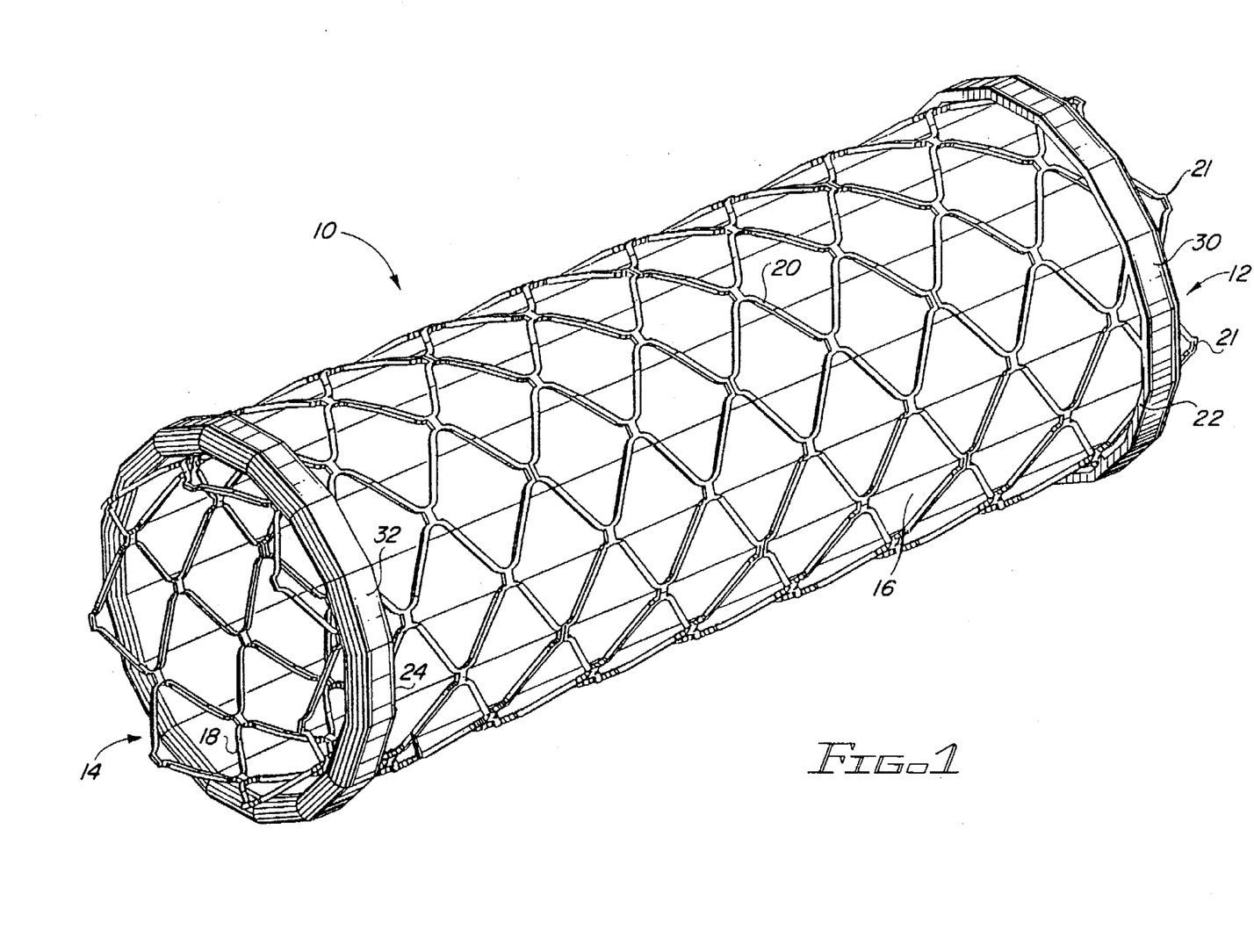
FIG. 1 is a perspective view of a first preferred embodiment of the dual supported intraluminal graft of the present invention comprising a tubular shaped configuration which includes a configuration of the support members.
Figures 2, 3, 4, 5:
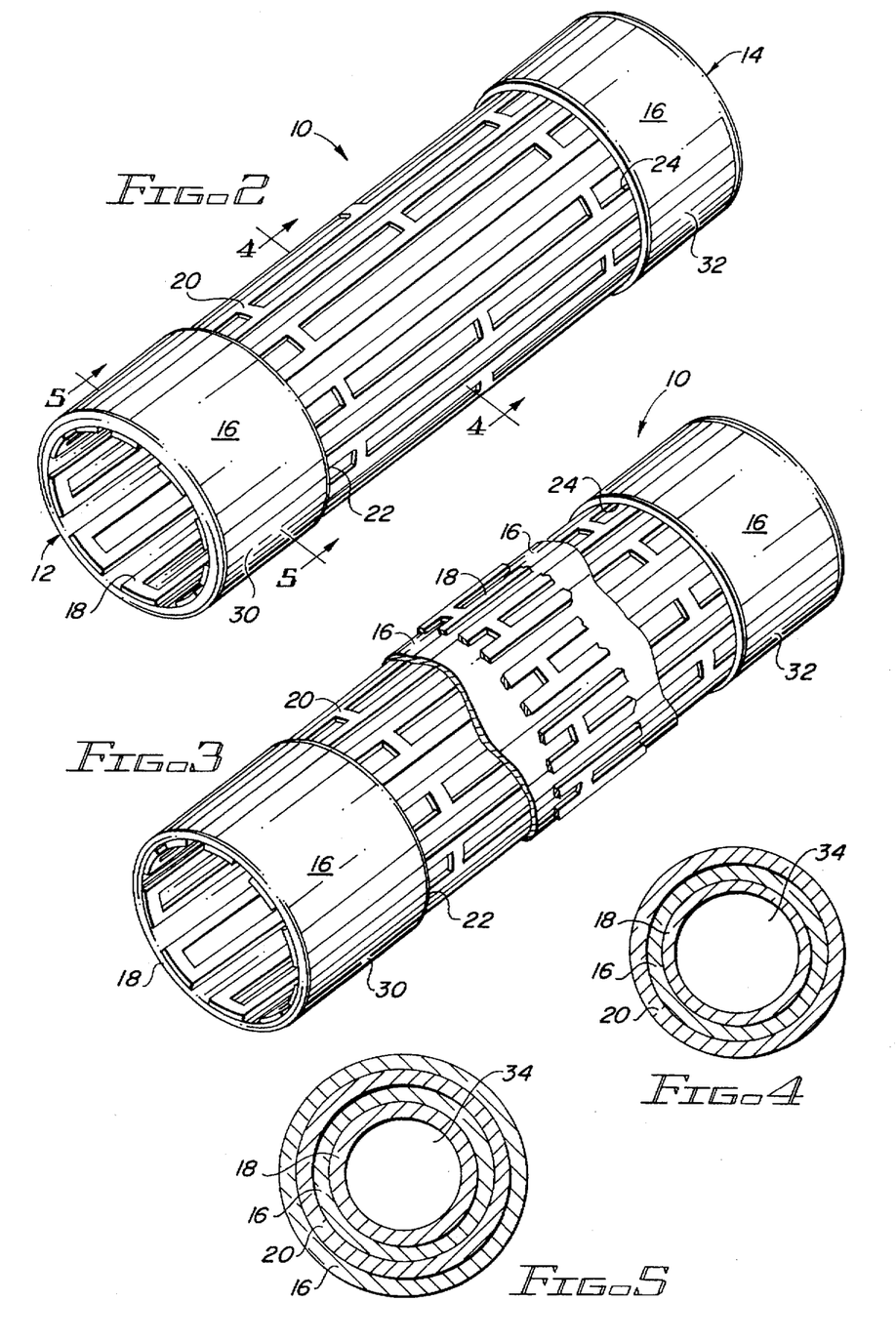
FIG. 2 is another perspective view of a first preferred embodiment of the dual supported intraluminal graft of the present invention comprising a tubular shaped configuration which includes a second configuration of the support members.
FIG. 3 is a perspective view of the first preferred embodiment of the present invention shown in FIG. 2 comprising the tubular shaped, dual supported intraluminal graft shown partially cut away to expose the underlying biocompatible member and underlying support member which comprise part of the intraluminal graft.
FIG. 4 is a cross-sectional view of the tubular shaped, dual supported intraluminal graft shown in FIG. 2 taken along line 4—4 of FIG. 2.
FIG. 5 is a cross-sectional view of the tubular shaped, dual supported intraluminal graft shown in FIG. 2 taken along line 5—5 of FIG. 2.

Referring now to the figures, where the reference numerals represent various elements of the present invention, a first preferred embodiment of the dual supported intraluminal graft 10 is illustrated in FIGS. 1 and 2. The first preferred embodiment of the dual supported intraluminal graft 10 of the present invention generally comprises a tubular shape having a first end 12 and a second end 14. The tubular shaped, dual supported intraluminal graft comprises a flexible tubular member 16, preferably comprised of a biocompatible material such as polytetrafluoroethylene (PTFE), which is loaded over a first tubular shaped support member 18, which preferably comprises a stent like that described in U.S. Pat. No. 4,733,665 issued to Palmaz. A second tubular shaped support member 20 is then loaded over the stent/graft combination, and the first and second ends 22,24 of the flexible tubular member 16 are folded back over the first and second ends 26,28 (not shown) of the second tubular shaped support member 20 to form first and second flaps 30,32 respectively.

Like the first tubular shaped support member 18, the second tubular shaped support member 20, preferably comprises a Palmaz stent. The first and second tubular shaped support members 18,20 may be comprised of any material having the strength and elasticity to permit radial expansion and resist radial collapse. Examples of such materials include silver, titanium, stainless steel, gold, and strong suitable plastics. FIG. 1 also illustrates barbs 21 which are formed from the first tubular shaped support member. The barbs 21 assist in securing and anchoring the dual supported intraluminal graft within a blood vessel.

After loading the tubular shaped members onto one another and folding back the ends of the PTFE tube, the tubular stent/graft/stent assembly is loaded onto a standard balloon catheter for expansion in vivo. The tubular shaped, dual supported intraluminal graft 10 of the present invention is designed to be used with any conventional balloon on a balloon catheter making the delivery system for the device simple and cost efficient.

FIG. 3 depicts a perspective view of the first preferred embodiment of the present invention comprising the tubular shaped, dual supported intraluminal graft illustrated in FIG. 2 shown partially cut away to expose the underlying members which comprise part of the intraluminal graft. The tubular shaped, dual supported intraluminal graft 10 includes a biocompatible flexible tubular member 16, preferably comprised of PTFE, which is sandwiched between two tubular shaped support members 18,20, which preferably comprise Palmaz stents, all of which are capable of being radially expanded. The biocompatible flexible tubular member 16 is greater in length than the first and second tubular shaped support members 18,20. This allows the first and second ends 22,24 of the biocompatible flexible tubular member 16 to be folded back onto the outer surface of the second tubular shaped support member 20, thereby encasing the first and second ends 26,28 (not shown) of the second tubular shaped support member 20 within the biocompatible flexible tubular member 16, and forming flaps 30,32 on the outer surface of the second tubular shaped support member 20.

The second tubular shaped support member 20 is cut away to reveal the underlying biocompatible tubular flexible member 16, which is further cut away to reveal the first tubular shaped support member 18. The first and second tubular shaped support members 18,20 may be of the same length. When the first and second tubular shaped support members 18,20 are of the same length, the second tubular shaped support member 20 shortens longitudinally as the center of the tubular shaped, dual supported intraluminal graft 10 expands during inflation of the balloon. The shortening of the second tubular shaped support member 20 allows the ends of the first tubular shaped support member 18 to flare outward beyond the first and second ends 26,28 (See FIGS. 6–7) of the second tubular shaped support member 20 and thereby function to assist in anchoring the tubular shaped, dual supported intraluminal graft 10 to the wall of a blood vessel. If flaring of the ends of the first tubular shaped support member 18 is undesirable, the flaring can be corrected by using a first tubular shaped support member 18 that is shorter in length than the second tubular shaped support member 20 when constructing the tubular shaped, dual supported intraluminal graft 10.

The first and second flaps 30,32 of the biocompatible tubular flexible member 16 and the first tubular shaped support member 18 of the tubular shaped, dual supported intraluminal graft 10 function to prevent the biocompatible tubular flexible member 16 from shortening away from the first and second ends 26,28 (See FIGS. 6–7) of the second tubular shaped support member 20. As a result, the biocompatible flexible member 16 does not compress to its center during expansion of the tubular shaped, dual supported intraluminal graft. The tubular shaped, dual supported intraluminal graft 10 of the present invention functions to solve several problems associated with existing tubular shaped vascular grafts including nonuniform expansion of the graft, graft shortening upon expansion, and suture tears or holes if sutures are needed to attached the graft to the support member.

A cross-sectional view taken along line 4—4 at the center of the tubular shaped, dual supported intraluminal graft 10 of the present invention illustrated in FIG. 2 is shown in FIG. 4. The first tubular shaped support member 18, preferably comprising a Palmaz stent or similarly constructed structure, forms the innermost layer of the tubular shaped, dual supported intraluminal graft 10 and surrounds the lumen 34 of the tubular, shaped dual supported intraluminal graft 10. The biocompatible flexible tubular layer 16, preferably comprised of PTFE, forms the middle layer located at the center of the tubular shaped, dual supported intraluminal graft 10. Finally, the second tubular shaped support member 20, which also preferably comprises a Palmaz stent or similarly constructed structure, forms the outermost layer located at the center of the tubular shaped, dual supported intraluminal graft 10.

FIG. 5 illustrates a cross-sectional view of the tubular shaped, dual supported intraluminal graft 10 shown in FIG. 2 taken along line 5—5 of FIG. 2 near the first end 12 of the intraluminal graft 10. The innermost layer is formed by the first tubular shaped support member 18 which surrounds the lumen 34 of the intraluminal graft 10. The next innermost layer is formed by the biocompatible flexible tubular member 16 which is covered by a support layer which is formed from the second tubular shaped support member 20. The outermost layer comprises a biocompatible layer which is formed by folding the first and second ends 22,24 of the biocompatible flexible tubular member over the first and second ends 26,28 (See FIGS. 6–7) of the second tubular shaped support member 20. As previously described, the tubular support members 18,20 preferably comprise Palmaz stents, or similarly constructed structures, but may be comprised of any material having the strength and elasticity to permit radial expansion and resist radial collapse.

Figure 6:
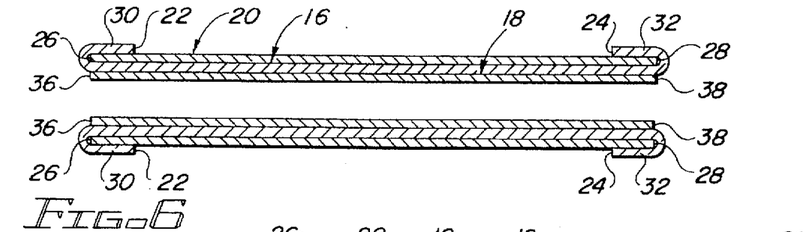
FIG. 6 is a longitudinal cross-section of a first preferred embodiment of the dual supported intraluminal graft of the present invention in an unexpanded state.
Figure 7:
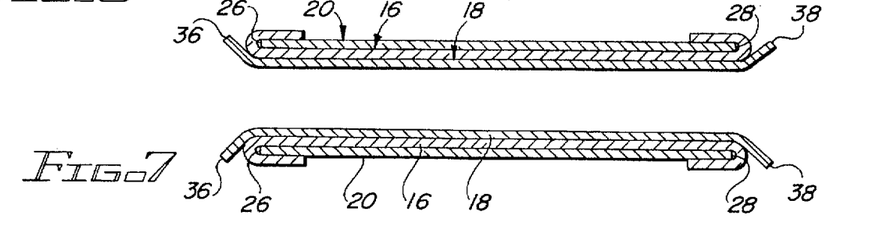
FIG. 7 is a longitudinal cross-section of a first preferred embodiment of the dual supported intraluminal graft of the present invention shown after expansion.

A longitudinal cross section of a first preferred embodiment of the tubular shaped, dual supported intraluminal graft prior to expansion is shown in FIG. 6. Prior to expansion, the flexible tubular member 16 is sandwiched between the first and second tubular support members 18,20 which are concentrically aligned with one another. The first and second ends 22,24 of the flexible tubular member 16 are folded back onto the outer surface of the second tubular support member 20 to form first and second flaps 30,32. FIG. 7 illustrates the longitudinal cross section of the intraluminal graft shown in FIG. 6 after expansion. During expansion with a balloon catheter, the dual supported intraluminal graft radially expands to form an expanded dual supported graft having anchoring means which are formed by the first and second ends 36,38 of the first tubular support member 18.

The following examples describe the preparation of various tubular shaped, dual supported intraluminal grafts in an attempt to determine the optimum length of the PTFE flaps and inflation pressure required to produce a tubular shaped, dual supported intraluminal graft which exhibits uniform expansion that results in inseparable layers. The examples are meant to be purely illustrative and nonlimiting.

All of the following examples were prepared by: (1) loading a 3 to 4 inch segment of graft material over the outside surface of a Palmaz stent; (2) loading the stent/graft configuration over a 3.18 millimeter (mm) outer diameter (OD) mandrel; (3) loading a second Palmaz stent over the outer surface of the graft material and aligning the ends with the first stent; (4) folding one end of the graft back over the outer surface of the second stent while applying enough pressure to remove any longitudinal slack or compression from the graft material; (5) cutting the first flap so that it is no longer than ½ the length of the stent; (6) folding the second end of the graft material back over the outer surface of the second stent and applying enough pressure to remove any longitudinal slack or compression from the graft material; (7) cutting the second flap so that it abuts the first flap; (8) marking each flap at a predetermined length from the end of the device; (9) cutting the flaps at the length marked; (10) gently removing the device from the mandrel; and (11) loading the device on a tapered catheter balloon and centering the device between the two radiopaque markers.

Further, all of the following examples were expanded in a 37 degrees Celcius (° C.) water bath using an ACS Indeflator Plus inflation device; OD and length measurements were taken using a Mitutoyo Digital Caliper; internal diameter (ID) measurements were taken using pin gauges and reflect minimum diameter; water temperature was maintained with a Cole-Parmer Polystet 12002 Series Immersion Heater and verified with a Fisher Thermometer; all of the stent devices used were Palmaz P394 stents (composed of 3166L stainless steel with a nominal length of 39 mm, a wall thickness of 0.0055 inches, and a nominal OD of 2.5 mm); the catheter balloons used were Medi-tech PEMT DC/10-3/8/100 in preconception examples and Examples 1 through 3, and Meditech PEMT DC/10-8/8/606 in Examples 4 and 5. A Mansfield 20–55 balloon was also used in Example 5.

In Example 3, a 5.0 mm tapered mandrel was used prior to crimping the device on a 3.18 mm mandrel. Differences in graft material used and final length of the folded flaps are indicated in the descriptions for each example. Any other deviations from the above procedure, along with individual results, are documented in the example descriptions as they occurred. Preconception examples consist of a single stent press-fit external to the graft material on a 3.18 mm mandrel.

Preconception Example A

A 3 mm ID Ultra Thin wall straight graft was used, and the flaps were cut to a length of 17 mm at one end and 10 mm at the other. At 6 atmospheres, the uncovered section of the stent expanded fully, and at 8 atmospheres the end of the device with the 10 mm long flap expanded fully. The pressure was increased to 10 atmospheres, whereupon, the balloon ruptured without fully expanding the 17 mm flap. After removing the device from the balloon, the following measurements were taken: (1) length was 30.65 mm; (2) OD was 9.57 mm; (3) length of the 10 mm flap was 3.89 mm; and (4) length of the 17 mm flap was 7.32 mm. Upon visual inspection of the device, ridges had formed in the lumen under the small flap, and the graft had recoiled away from the inner surface of the stent.

Preconception Example B

The same graft was used as in Preconception Example A, but both flaps were cut to a length of 5 mm. Again, the initial expansion occurred in the uncovered section of the stent. Full expansion of the device occurred at 7 atmospheres. However, the graft pulled away from the internal surface of the stent and stuck to the balloon when the balloon was deflated and migration of the graft again caused ridges along the lumen. Upon deflation of the balloon, it was difficult to separate the graft from the balloon. An additional stent internal to the graft was suggested to prevent the graft from recoiling during deflation. The remaining examples incorporate this suggestion.

Example 1

In order to offset the pressure required to expand 2 concentric stents, a 3 mm Thinwall High Porosity Straight 50 micron graft was used and both flaps were cut to a length of 5 mm. The balloon was rapidly inflated to 7 atmospheres and the device fully expanded. However, it was felt that full expansion of the device could have been achieved at a lower pressure if the balloon had been inflated more slowly. Visual inspection of the device after removal from the balloon revealed a tear in the graft material sandwiched between the two stents. It is felt that this was due to an unseen flaw in the graft and not due to the expansion pressure.

Example 2

The same graft material in Example 1 was used for Example 2, but was visibly inspected prior to loading, and both flaps were cut to a length of 8 mm. The device was fully expanded at 5.5 atmospheres. After removal from the balloon, the ID was 7.75 mm. This example was deemed a success.

Example 3

It was decided to use a larger ID graft to determine if the device could be successfully crimped on a P394 stent and fully expanded. A 4 mm High Porosity micron graft was used and both flaps were cut to a length of 8 mm. Due to the larger diameter of the graft material, a 5.0 mm tapered mandrel was used to pre-dilate the second stent. The second stent was loaded over the 4 mm graft; the outer stent and graft were loaded on the 5.0 mm tapered mandrel; the end of the graft over the larger mandrel diameter was folded back over the outside surface of the second stent; the stent/graft was removed, reversed, and reloaded on the 5.0 mm tapered mandrel; the end of the graft now over the larger mandrel diameter was folded back over the outer surface of the second stent and removed, and both flaps were cut to the length of 8 mm. This partial assembly had an OD of 5.89 mm, an ID of 5.1 mm, and an overall length of 37.81 mm. The first stent was loaded inside the stent graft and the whole configuration was loaded on the 5.0 mm tapered mandrel to press-fit the inner stent to the graft material in order to prevent damage to, or migration of, the graft during crimping. The device was crimped down on a 3.18 mm mandrel by gently pressing and rolling in a longitudinally slit piece of tygon tubing. After crimping, the flaps were loose. The profile of the device after loading the device on balloon was 4.3 mm OD. Initial expansion was seen in the center at 3.5 atmospheres. At 5 atmospheres, the flaps were tight, and at 8 atmospheres the distal OD was 9.3 mm but the proximal OD was 6.3 mm due to device placement on the balloon being slightly off center towards the proximal end. The balloon was deflated and the device was repositioned toward the distal end. At 8 atmospheres, the balloon ruptured during reinflation. After removal from balloon, the OD was 8.9 mm, the ID was 7.24 mm, and the overall length was 34.08 mm. The device was reloaded on the same type of balloon and the balloon was inflated to 8 atmospheres with a resulting OD of 9.3 mm. The balloon was then inflated to 9 atmospheres with a resulting OD of 9.4 mm. After removal from the balloon, the ID was 7.54 mm; the OD was 8.99 mm; the length was 32.63 mm; but the device contained a slight bottle neck at the proximal end.

Example 4

A 3 mm Thin Wall Straight graft material from the third example described above, with a low expansion pressure was used for Example 4; both flaps were cut to a length of 3 mm and a 10 mm×8 cm balloon was used. At 1 atmosphere, the tapered ends of the balloon inflated and the balloon hot-dogged; at 4 atmospheres, both ends of the device expanded; at 5 atmospheres, the center of the device expanded; at 6 atmospheres, the OD was 8.3 mm; at 7 atmospheres, the OD was 8.8 mm; and at 8 atmospheres, the balloon ruptured. After removing the device from the balloon, the OD was 9.06 mm.

Example 5

A 3 mm Thin Wall Straight graft was used; both flaps were cut to a length of 2.33 mm; and the device was loaded on a 10 mm×4 cm balloon. At 8 atmospheres, the OD was 8.13 mm, but at 10 atmospheres, the balloon burst. The device was loaded on a 10 mm×8 cm balloon which ruptured at 8 atmospheres. After removal from the balloon the OD was 8.51 mm and exhibited a hotdog shaped profile. The device was loaded on a 20 mm balloon, but attempt to remove the hotdogging was unsuccessful. After removal from the balloon, the OD was 9.2 mm.

As noted from the above examples, a 3 mm ID thin walled High Porosity PTFE graft sandwiched between two P-394 "PALMAZ" stents and expanded at 5.5 atmospheres, at 37 degrees Celsius, results in a uniformly expanded tubular shaped, dual supported intraluminal graft having stent and graft and stent layers that are inseparable. The stent and graft design may be modified to decrease the expansion pressure.

Figures 8, 9, 10:
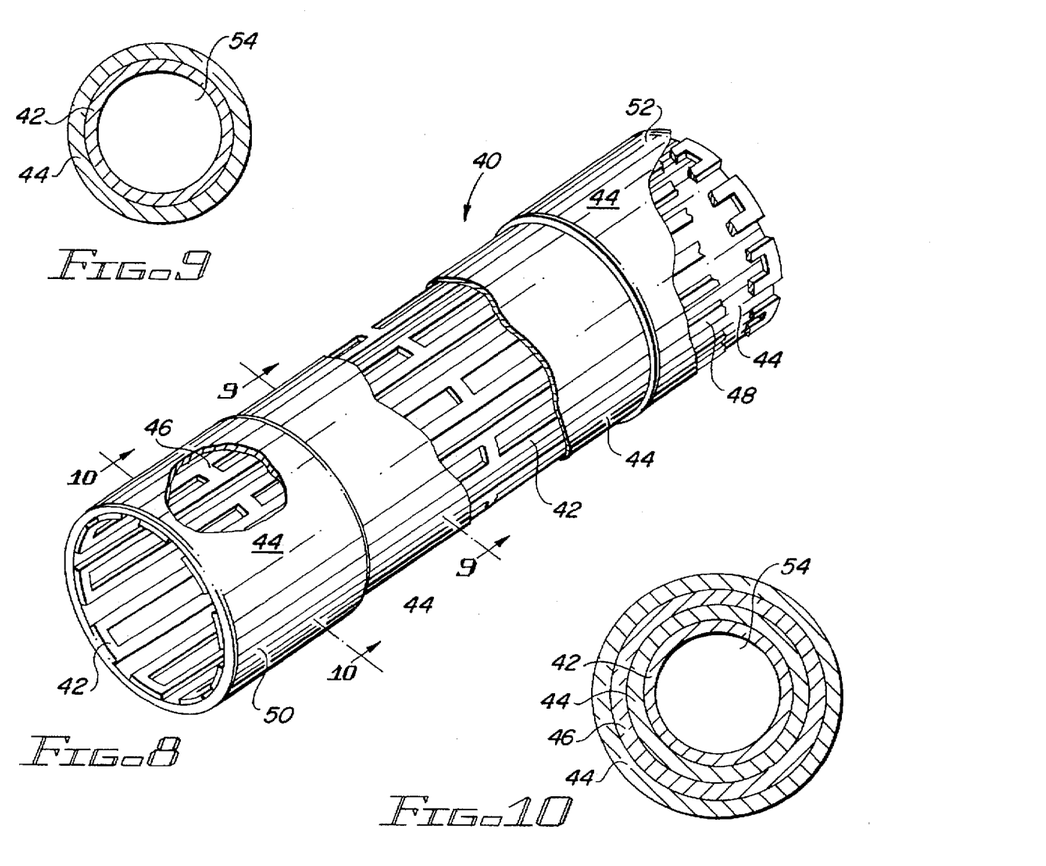
FIG. 8 is a perspective view of a second embodiment of the tubular shaped, dual supported intraluminal graft configuration of the present invention with areas shown partially cut away to expose the underlying layers which comprise the intraluminal graft.
FIG. 9 is a cross-sectional view of the tubular shaped, dual supported intraluminal graft shown in FIG. 8 taken along line 9—9 of FIG. 8.
FIG. 10 is a cross-sectional view of the tubular shaped, dual supported intraluminal graft shown in FIG. 8 taken along line 10—10 of FIG. 8.

A second embodiment of the tubular shaped, dual supported intraluminal graft 40 of the present invention is illustrated in FIGS. 8–10. The tubular shaped, dual supported intraluminal graft 40 comprises a first elongated tubular support member 42 which is covered by a flexible tubular member 44. The first elongated tubular support member 42 preferably comprises a Palmaz stent but may comprise other structural configurations which are comprised of any material having the strength and elasticity to permit radial expansion and resist radial collapse. The flexible tubular member 44 is preferably comprised of a biocompatible material such as PTFE. The tubular shaped, dual supported intraluminal graft 40 further comprises a pair of first and second short cylindrical support members 46,48 which are loaded over the flexible tubular member 44 and positioned at opposite ends of the flexible tubular member 44. The ends of the flexible tubular member 44 are folded back over the outer surface of the first and second short cylindrical support members 46,48 thereby forming first and second flaps 50,52, respectively, which encase at least the outermost ends of each of the first and second short cylindrical support members 46,48 within the flexible tubular member 44. Further, as illustrated in FIG. 8, the entire first and second short cylindrical support members 46,48 may be covered by the first and second flaps 50,52 of the flexible tubular member 44.

As shown in the cross-sectional view depicted in FIG. 9, which is taken along line 9—9 of FIG. 8, the center portion of the second embodiment of the tubular shaped, dual supported intraluminal graft 40 includes the elongated tubular support member 42, preferably comprising a Palmaz stent, which surrounds the lumen 54 of the tubular shaped, dual supported intraluminal graft 40 of the present invention. The flexible tubular member 44, preferably comprised of PTFE, surrounds the elongated tubular support member 42 and forms the outermost layer of the tubular shaped, dual supported intraluminal graft 40.

FIG. 10 illustrates a cross-sectional view of the tubular shaped, dual supported intraluminal graft 40 shown in FIG. 8 taken along line 10—10 of FIG. 8 near an end of the intraluminal graft 40. The innermost layer is formed by the elongated tubular support member 42 which surrounds the lumen 54 of the intraluminal graft 40. The next innermost layer is formed by the flexible tubular member 44 which is covered by a support layer which is formed from the first short cylindrical support member 46. The outermost layer comprises a biocompatible layer which is formed by folding an end of the flexible tubular member 44 over the outermost end of the first short cylindrical shaped support member 46 and back over the outer surface of the first short tubular shaped cylindrical member 46.

A third embodiment of the tubular shaped, dual supported intraluminal graft 60 of the present invention is illustrated in FIGS. 11—14. The tubular shaped, dual supported intraluminal graft 60 comprises a biocompatible flexible tubular member 62, preferably comprised of PTFE, having a first end 64 and a second end 66, a pair of first and second shortened cylindrical support members 68,70, and a pair of third and fourth shortened cylindrical support members 72,74. The pair of third and fourth shortened cylindrical support members 72,74 are located near opposite ends of the biocompatible tubular flexible member 62, respectively, and are concentrically retained within the interior of the biocompatible flexible tubular member 62. The pair of first and second shortened cylindrical support members 68,70 are also located near opposite ends of the biocompatible flexible tubular member 62, respectively, but are concentrically positioned about the exterior surface of the biocompatible flexible tubular member 62 such that the pair of first and second shortened cylindrical support members 68,70 directly overlap the pair of third and fourth shortened cylindrical support members 72,74, respectively, with only the biocompatible flexible tubular member 62 contained between them. The first cylindrical support member 68 is not shown in FIG. 11 in that it is completely encased within the biocompatible flexible tubular member 62.

Figures 11, 12, 13, 14:
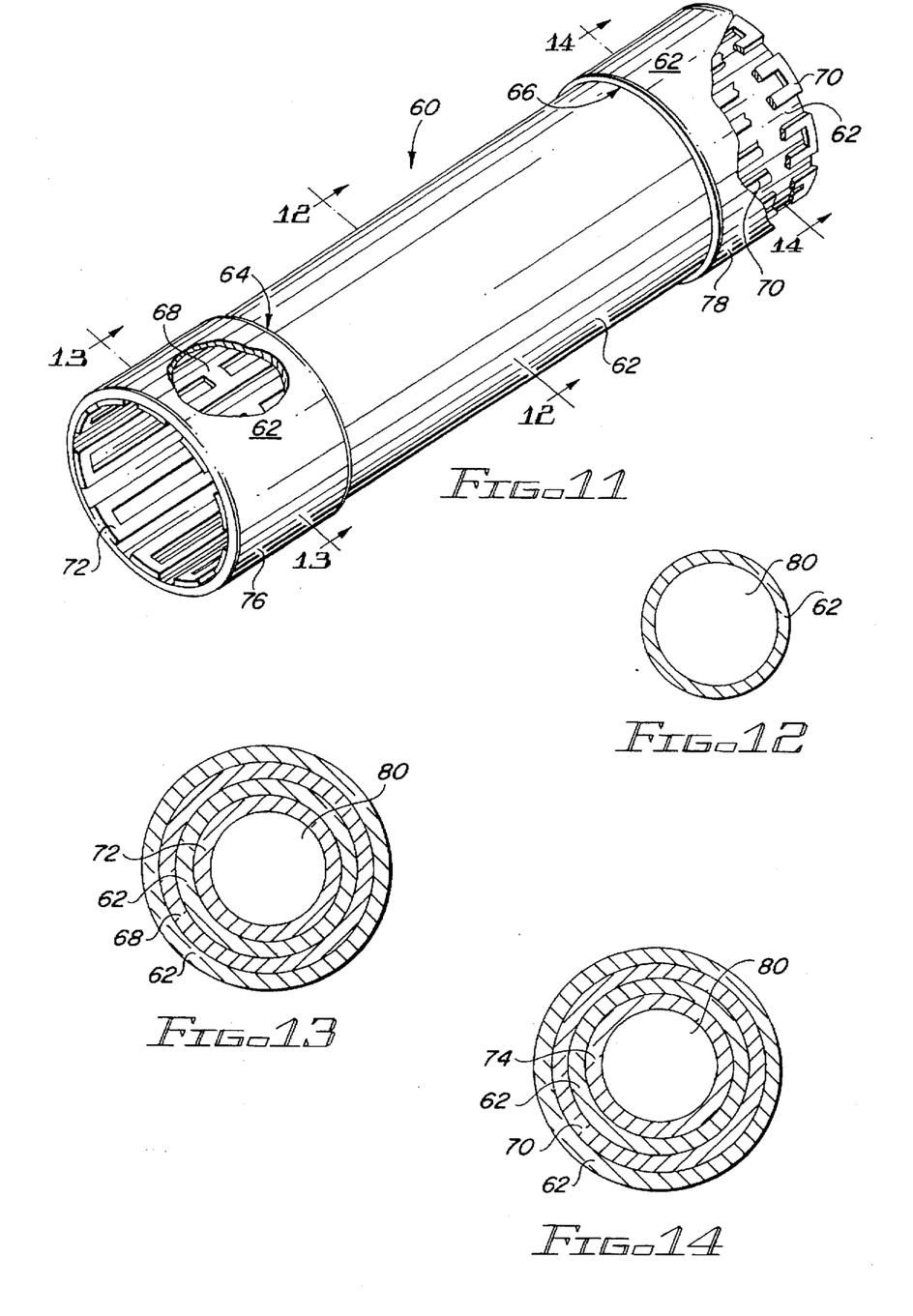
FIG. 11 is a perspective view of a third embodiment of the tubular shaped, dual supported intraluminal graft configuration of the present invention shown partially cut away to expose the underlying layers which comprise the intraluminal graft.
FIG. 12 is a cross-sectional view of the tubular shaped, dual supported intraluminal graft shown in FIG. 11 taken along line 12—12 of FIG. 11.
FIG. 13 is a cross-sectional view of the tubular shaped, dual supported intraluminal graft shown in FIG. 11 taken along line 13—13 of FIG. 11.
FIG. 14 is a cross-sectional view of the tubular shaped, dual supported intraluminal graft shown in FIG. 11 taken along line 14—14 of FIG. 11.

The pairs of shortened cylindrical support members 68,70 72,74 preferably comprise short Palmaz stents or similarly structured configurations which are comprised of a suitable material having sufficient strength and elasticity to permit radial expansion and resist radial collapse. Further, the first and second ends 64,66 of the biocompatible flexible tubular member 62 may be folded back over the outside surface of the pair of first and second shortened cylindrical support members 68,70 to form first and second flaps 76,78, as illustrated in FIG. 11, thereby encasing the outermost ends of the first and second shortened cylindrical support members 68,70 within the biocompatible flexible tubular member 62. Also, as illustrated in FIG. 11, the first and second shortened cylindrical support members 68,70 may be entirely covered by the first and second flaps 76,78 of the biocompatible flexible tubular member 62.

As shown in the cross-sectional view depicted in FIG. 12 which is taken along line 12—12 of FIG. 11, the center portion of the third embodiment of the tubular shaped, dual supported intraluminal graft 60 simply comprises a lumen 80 which is surrounded by the biocompatible flexible tubular member 62. FIG. 13 illustrates a cross-sectional view of the tubular shaped, dual supported intraluminal graft 60 shown in FIG. 11 taken along line 13—13 of FIG. 11 near an end of the intraluminal graft 60. The innermost layer is formed by the third shortened cylindrical support member 72 which surrounds the lumen 80 of the intraluminal graft 60. The next innermost layer is formed by the biocompatible flexible tubular member 62 which is covered by a support layer which is formed from the first shortened cylindrical support member 68. The outermost layer comprises a biocompatible layer which is formed by folding the first end 64 of the biocompatible flexible tubular member 62 over the outermost end of the first shortened cylindrical support member 68 and back over the outer surface of the first shortened cylindrical support member 68.

FIG. 14 shows a cross-sectional view of the tubular shaped, dual supported intraluminal graft 60 shown in FIG. 11 taken along line 14—14 of FIG. 11 near the opposite end of the cross-sectional view of the intraluminal graft 60. The innermost layer is formed by the fourth shortened cylindrical support member 74 which surrounds the lumen 80 of the intraluminal graft 60. The next innermost layer is formed by the biocompatible flexible tubular member 62 which is covered by a support layer which is formed from the second shortened cylindrical support member 70. The outermost layer comprises a biocompatible layer which is formed by folding the second end 66 of the biocompatible flexible tubular member 62 over the outermost end of the second shortened cylindrical support member 70 and back over the outer surface of the second shortened cylindrical support member 70.

A fourth embodiment of the tubular shaped, dual supported intraluminal graft 90 of the present invention is illustrated in FIGS. 15–19. The tubular shaped, dual supported intraluminal graft 90 comprises a biocompatible flexible tubular member 92, preferably comprised of PTFE, having a first end 94 and a second end 96, a first series of shortened cylindrical support members which include first, second and third shortened cylindrical members 98,100,102, and a second series of shortened cylindrical support members which include fourth, fifth and sixth shortened cylindrical members 104,106,108. The fourth and fifth shortened cylindrical support members 104,106 are concentrically retained within the interior of the biocompatible flexible tubular member 92 near opposite ends of the biocompatible flexible tubular member 92, respectively, while the sixth shortened cylindrical support member 108 is concentrically retained within the interior of the biocompatible flexible tubular member 92 between the fourth and fifth shortened cylindrical support members 104,106. The first and second shortened cylindrical support members 98,100 are concentrically positioned about the exterior surface of the biocompatible flexible tubular member 92 near opposite ends of the biocompatible flexible tubular member 92, respectively, while the third shortened cylindrical support member 102 is concentrically positioned about the exterior surface of the biocompatible flexible tubular 92 between the first and second shortened cylindrical support members 98,100. The first, second and third shortened cylindrical support members 98,100.102 are superimposed over the fourth, fifth, and sixth shortened cylindrical support members, respectively, with the biocompatible flexible tubular member 92 sandwiched between each resulting superimposed pair of shortened cylindrical support members.

Figures 15, 16, 17, 18, 19:
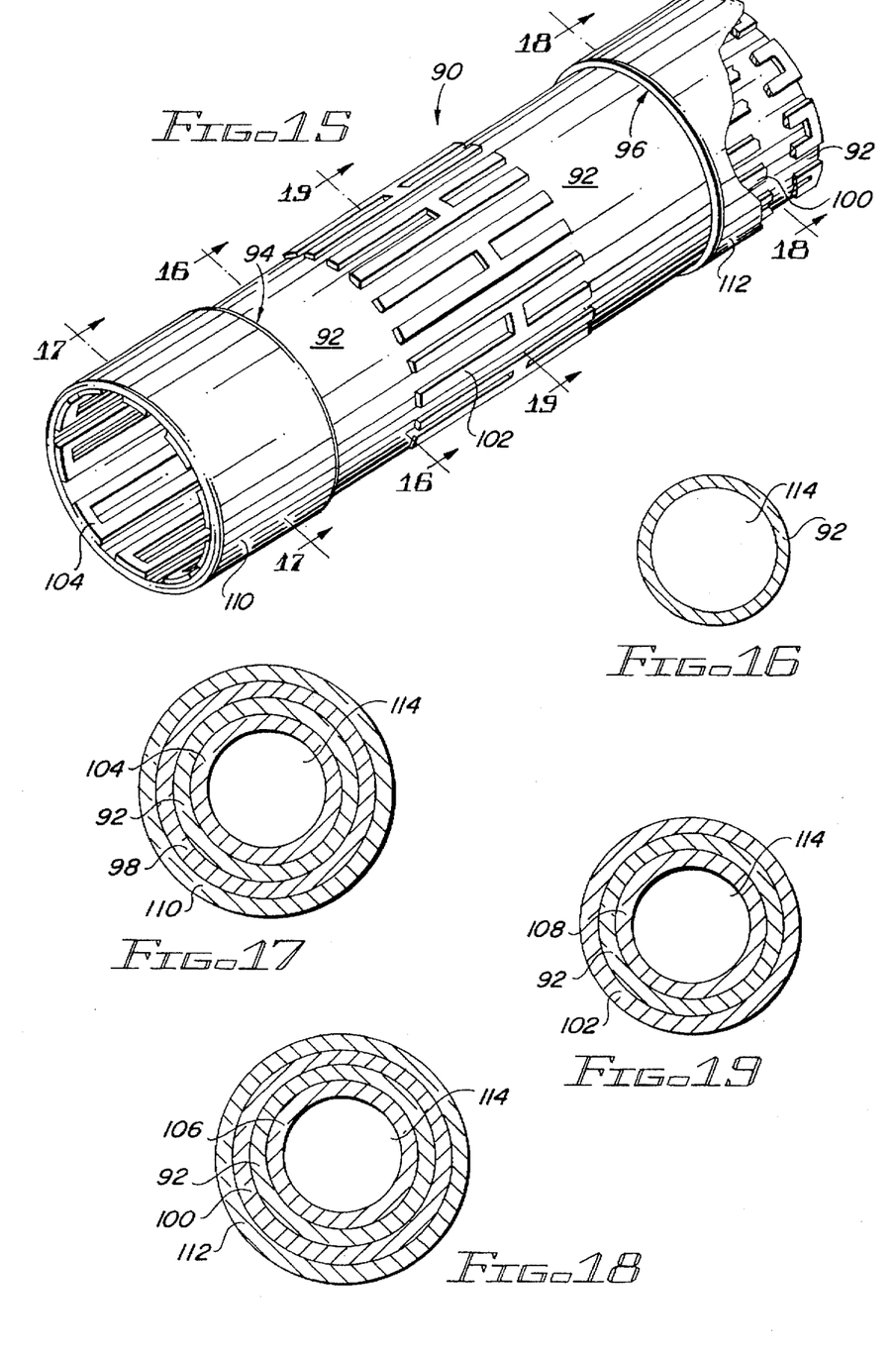
FIG. 15 is a perspective view of a fourth embodiment of the tubular shaped, dual supported intraluminal graft of the present invention shown partially cut away to expose the underlying layers which comprise the graft.
FIG. 16 is a cross-sectional view of the tubular-shaped, dual supported intraluminal graft shown in FIG. 15 taken along line 16—16 of FIG. 15.
FIG. 17 is a cross-sectional view of the tubular-shaped, dual supported intraluminal graft shown in FIG. 15 taken along line 17—17 of FIG. 15.
FIG. 18 is a cross-sectional view of the tubular-shaped, dual supported intraluminal graft shown in FIG. 15 taken along line 18—18 of FIG. 15.
FIG. 19 is a cross-sectional view of the tubular-shaped, dual supported intraluminal graft shown in FIG. 15 taken along line 19—19 of FIG. 15.

All of the shortened cylindrical support members 98,100, 102,104,106,108 preferably comprise short Palmaz stents or similarly structured configurations which are comprised of a suitable material having sufficient strength and elasticity to permit radial expansion and resist radial collapse. Further, the first and second ends 94,96 of the biocompatible flexible tubular member 92 are folded back onto the outer surfaces of the first and second shortened cylindrical support members 98,100, respectively, to form first and second flaps 110,112 thereby encasing the outermost ends of the first and second shortened cylindrical members 98,100 within the biocompatible flexible tubular member 92. Also, as illustrated in FIG. 15, the fourth and fifth shortened cylindrical members 104,106 may be entirely covered by the first and second flaps 110,112 of the biocompatible flexible tubular member 92. This configuration of the fourth embodiment results in a tubular shaped articulating intraluminal graft which has a series of dual stent supported sections which are separated by entirely unsupported sections of the biocompatible flexible tubular member 92. This embodiment of the dual supported intraluminal graft provides flexibility during placement while still providing rigid support after deployment.

The cross-sectional view depicted in FIG. 16, which is taken along line 16—16 of FIG. 15, illustrates an unsupported section of the articulating dual supported intraluminal graft shown in FIG. 15. This section of the graft simply comprises a lumen 114 which is surrounded by the biocompatible flexible tubular member 92.

FIGS. 17 and 18 illustrate cross-sectional views taken along line 17—17 and line 18—18 of FIG. 15, respectively. These cross-sectional views illustrate the layers which comprise the end sections of the articulating dual supported intraluminal graft. In FIGS. 17 and 18, the innermost layer is formed by the fourth and fifth shortened cylindrical support members 104,106, respectively, which surround the lumen 114 of the articulating dual supported intraluminal graft. The next innermost layer in both FIGS. 17 and 18 is formed by the biocompatible flexible tubular member 92 which is then covered by a support layer which is formed from the first and second shortened cylindrical support members 98,100, respectively. Finally, the outermost layers in FIGS. 17 and 18 comprise a biocompatible layer which is formed by folding the first and second ends 94,96 of the biocompatible flexible tubular member 92 over the outermost ends of the first and second shortened cylindrical support members 98,100, respectively, and back over the outer surface of the first and second shortened cylindrical support members 98,100, respectively.

FIG. 19 shows a cross-sectional view taken along line 19—19 of FIG. 15. This cross-sectional view illustrates the layers which are present in the center dual supported section of the articulating dual supported intraluminal graft. The innermost layer is formed from the sixth shortened cylindrical support member 108 which surrounds the lumen 114 of the articulating dual supported intraluminal graft. The middle layer comprises a biocompatible material which is formed from the biocompatible flexible tubular member 92 and the outermost layer is formed from the third shortened cylindrical support member 102.

It should be understood by those skilled in the relevant field of art that each of the previously described embodiments of the tubular shaped, dual supported intraluminal graft may also exist without folding back the PTFE tubular member to form flaps on the ends of the intraluminal graft. Further, all of the previously described compositions for the members which comprise the various embodiments of the tubular shaped, dual supported intraluminal graft are preferably expandable.

While the invention has been described with reference to preferred embodiments thereof, the description is for illustrative purposes only and is not to be construed as limiting the scope of the invention. Various modifications and changes may be made by those skilled in the art without departing from the true spirit of the scope of the invention as defined by the appended claims.

We claim:

1. A radially expandable dual supported intraluminal graft comprising:
   a first radially expandable tubular support member;
   a second radially expandable tubular support member having first and second opposing ends and concentrically positioned about the first radially expandable tubular support member; and
   an expanded polytetrafluoroethylene tubular member, interdisposed between the first and second radially expandable tubular support members, having first and second opposing ends coupled to the first and second opposing ends of the second radially expandable tubular support member.

2. The radially expandable dual supported intraluminal graft of claim 1 wherein the first and second radially expandable tubular support members are made of a biocompatible material selected from the group of silver, titanium, stainless steel, and gold.

3. The radially expandable dual supported intraluminal graft of claim 1 wherein the expanded polytetrafluoroethylene tubular member is characterized by a microporous microstructure having an average internodal distance within a range of 10 to 90 microns.

4. The radially expandable dual supported intraluminal graft of claim 1 wherein the at least one of the first and second opposing ends of the expanded polytetrafluoroethylene tubular member is evertedly folded over at least one of the first and second opposing ends of the second radially expandable tubular support member such that the at least one of the first and second opposing ends of the second radially expandable tubular support member is annularly covered by the expanded polytetrafluoroethylene tubular member and the at least one of the first and second ends of the expanded polytetrafluoroethylene tubular member is supported about the at least one of the first and second ends of the second radially expandable tubular support member.

5. The radially expandable dual supported intraluminal graft of claim 4 wherein the at least one folded back first and second ends of the expanded polytetrafluoroethylene tubular member comprises a length of up to one-half a length of the second tubular shaped support member.

6. The radially expandable dual supported intraluminal graft of claim 1 wherein the second tubular support member further comprises first and second ring members positioned at the first and second ends of said first tubular shaped support member and in spaced apart relationship to one another.

7. The radially expandable dual supported intraluminal graft of claim 6 wherein the first and second ends of the expanded polytetrafluoroethylene tubular member are evertedly folded onto outer surfaces of the first and second ring members which are thereby at least partially enclosed by the evertedly folded first and second ends of the expanded polytetrafluoroethylene tubular material.

8. The radially expandable dual supported intraluminal graft of claim 7 wherein the evertedly folded first and second ends of the expanded polytetrafluoroethylene tubular member each comprise a length of up to one-half a length of the first and second ring members.

9. The radially expandable dual supported intraluminal graft of claim 6 wherein said first tubular support member comprises third and fourth ring members concentrically positioned about the first and second ring members comprising the second tubular support member and the expanded polytetrafluoroethylene tubular member further comprises an intermediate region along a longitudinal axis of the intraluminal graft which is unsupported by any of the first and second ring members comprising the second tubular support member and any of the third and fourth ring members comprising the first tubular support member.

10. The radially expandable dual supported intraluminal graft of claim 9 wherein the expanded polytetrafluoroethylene tubular member is evertedly folded over the first and second ring members comprising the second tubular support member.

11. The radially expandable dual supported intraluminal graft of claim 9 further comprising at least one pair of concentrically positioned cylindrical support members positioned intermediate the first and second ring members comprising each of the first and second tubular support members and in spaced apart relationship thereto, the expanded polytetrafluoroethylene tubular member being interdisposed between the pair of concentrically positioned cylindrical support members.

12. The radially expandable dual supported intraluminal graft of claim 11 wherein the first and second ends of the expanded polytetrafluoroethylene tubular member are evertedly coupled to the first and second ring members of each of the first and second tubular support members.

13. The radially expandable dual supported intraluminal graft of claim 1 wherein the first and second tubular support members are each comprised of a plurality of concentric pairs of support members co-axially aligned and in spaced apart relationship with one another along a longitudinal axis of the intraluminal graft and the expanded polytetrafluoroethylene tubular member is interdisposed and retained between the plurality of concentric pairs of support members thereby imparting flexibility along the longitudinal axis of the intraluminal graft.

14. The radially expandable dual supported intraluminal graft of claim 13 wherein the first and second ends of the polytetrafluoroethylene tubular member are evertedly folded over first and second ends of opposing end pairs of the plurality of concentric pairs of support members comprising each of the first and second cylindrical shaped support members.

15. The radially expandable dual supported intraluminal graft of claim 1 wherein the first and second radially expandable tubular support members are made of a biocompatible plastic having sufficient hoop strength and radial elasticity to enable uniform radial expansion without radial collapse under physiological conditions.

16. A process for making a tubular radially expandable dual supported intraluminal graft comprising the steps of:
   a) positioning an expanded polytetrafluoroethylene tubular member having a microporous microstructure of nodes interconnected by fibrils concentrically over and in intimate contact with a first radially expandable stent member;

b) concentrically positioning a second radially expandable stent member over and in intimate contact with the expanded polytetrafluoroethylene tubular member; and c) applying a positive pressure to said biocompatible flexible tubular member and said first and second tubular shaped support members such that all of said members are inseparable.

17. The process of claim 16, further including the step of everting at least one end of the expanded polytetrafluoroethylene tubular member over and onto an outer end surface of at least one end of said second radially expandable stent member thereby covering said at least one end of said second radially expandable stent with the everted at least one end of the expanded polytetrafluoroethylene tubular member.

18. A radially expandable dual supported intraluminal graft comprising:

a biocompatible flexible tubular member having a first end, a second end, an inner surface and an outer surface;

a first tubular shaped support assembly comprising at least two cylindrical shaped support members concentrically positioned relative to one another at a first end of the biocompatible flexible tubular member, one of the at least two cylindrical shaped support members being in intimate contact with an inner surface of the biocompatible flexible tubular member and a second of the at least two cylindrical shaped support members being in intimate contact with the outer surface of the biocompatible flexible tubular member;

a second tubular shaped support assembly comprising at least two cylindrical shaped support members concentrically positioned relative to one another at the second end of the biocompatible flexible tubular member, one of the at least two cylindrical shaped support members being in intimate contact with an inner surface of the biocompatible flexible tubular member and a second of the at least two cylindrical shaped support members being in intimate contact with the outer surface of the biocompatible flexible tubular member; and a third tubular shaped support assembly comprising at least two cylindrical shaped support members concentrically positioned relative to one another intermediate the first and second ends of the biocompatible flexible tubular member, one of the at least two cylindrical shaped support members being in intimate contact with an inner surface of the biocompatible flexible tubular member and a second of the at least two cylindrical shaped support members being in intimate contact with the outer surface of the biocompatible flexible tubular member.

19. The radially expandable dual supported intraluminal graft of claim 18, wherein at least a portion of the first and second ends of the biocompatible flexible tubular member are evertedly folded over the first and second cylindrical shaped support assemblies such that one of the at least two cylindrical shaped support members comprising each of the first and second cylindrical shaped support assemblies is at least partially covered by the everted portions of the biocompatible flexible tubular member.

20. The radially expandable dual supported intraluminal graft of claim 19, wherein the everted portions of the biocompatible flexible tubular member each comprise a length no greater than about one-half longitudinal length of the first and second cylindrical shaped support assemblies.

21. The radially expandable dual supported intraluminal graft of claim 20 wherein each of the first, second and third cylindrical support assemblies are positioned substantially equidistantly along a longitudinal axis of the biocompatible flexible tubular member.

22. The radially expandable dual supported intraluminal graft of claim 21, wherein one of the first and second cylindrical members of each of the first and second cylindrical support assemblies is substantially encased within the everted first and second ends of the biocompatible flexible tubular member.

* * * * *